United States Patent [19]

Paul

[11] 4,447,603

[45] May 8, 1984

[54] SUBSTITUTED-6-N-PROPYL-8-METHYLIMIDAZO[1,5-D]-AS-TRIAZIN-4-(3H)-ONES

[75] Inventor: Rolf Paul, River Vale, N.J.

[73] Assignee: American Cyanamid Company, Stamford, Conn.

[21] Appl. No.: 231,196

[22] Filed: Feb. 4, 1981

[51] Int. Cl.³ .................... A61K 31/53; C07D 487/04
[52] U.S. Cl. .................................... 544/184; 424/45; 424/249
[58] Field of Search .................. 544/184; 424/45, 249

[56] References Cited

U.S. PATENT DOCUMENTS 4,107,307 8/1978 Paul .................................... 424/249

Primary Examiner—Robert W. Ramsuer
Attorney, Agent, or Firm—Edward A. Conroy, Jr.

[57] ABSTRACT

This disclosure describes new compounds and compositions of matter useful as anti-asthmatic agents and the method of meliorating asthma in mammals therewith, the novel active ingredients of said compositions of matter being certain 1-substituted-6-n-propyl-8-methylimidazo [1,5-d]-as-triazin-4(3H)-ones and/or the pharmacologically acceptable acid-addition salts thereof.

7 Claims, No Drawings

SUBSTITUTED-6-N-PROPYL-8-METHYLIMIDAZO[1,5-D]-AS-TRIAZIN-4-(3H)-ONES

BRIEF SUMMARY OF THE INVENTION

This invention relates to new organic compounds and, more particularly, is concerned with novel 1-substituted-6-n-propyl-8-methylimidazo[1,5-d]-as-triazin-4(3H)-ones which may be represented by the following structural formula:

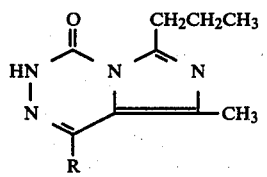

wherein R is methyl, ethyl or n-propyl.

The organic bases of this invention form non-toxic acid-addition salts with a variety of pharmacologically acceptable organic and inorganic salt-forming reagents. Thus, acid-addition salts, formed by a mixture of the organic free base with one or more equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

DETAILED DESCRIPTION OF THE INVENTION

The novel compounds of the present invention may be readily prepared as set forth in the following reaction scheme:

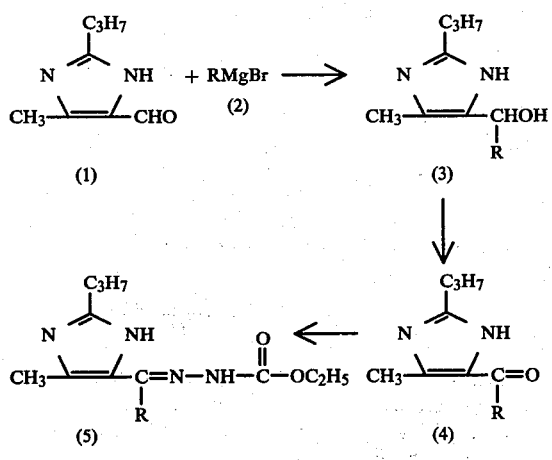

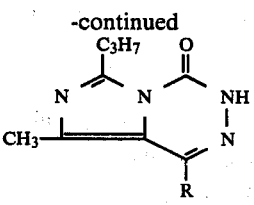

wherein R is a hereinabove defined. In accordance with the above reaction scheme, 2-n-propyl-5-methyl-4-imidazolecarboxaldehyde (1) is reacted with an alkylmagnesium bromide (2) in tetrahydrofuran under an inert atmosphere (argon, nitrogen, etc.) at 0°–10° C. for several hours. Acidification of the reaction mixture followed by saturation with ammonium chloride provides the α-alkyl-2-n-propyl-5-methyl-4-imidazolemethanol (3). Oxidation of (3) with Jones' reagent in acetone at 20°–30° C. for a few hours provides the 2-n-propyl-5-methyl-4-imidazolylketone (4) which is isolated by basification of the reaction mixture followed by extraction with ethyl acetate. Condensation of (4) with ethyl carbazate in n-butanol containing a few drops of glacial acetic acid under reflux for several hours provides (5) which is isolated by evaporation of the reaction mixture. Cyclization of (5) is accomplished in diphenyl ether at 150°–250° C. for 15–45 minutes to provide the novel compounds of the present invention (6). Isolation of (6) is achieved by dilution of the reaction mixture with petroleum ether or by extraction of the reaction mixture with 10% aqueous hydrochloric acid. The acid extract is neutralized with potassium carbonate and the product extracted with solvents such as chloroform or ethyl acetate.

The novel compounds of the present invention are highly active as anti-asthmatic agents as will be demonstrated hereinbelow. Their activity in this respect is far superior to the closest known prior art compound, 6-n-propyl-8-methylimidazo[1,5-d]-as-triazin-4(3H)-one, which is disclosed in Example 83 of U.S. Pat. No. 4,107,307.

The bronchospasm of allergic asthma is a consequence of the release of mediators, such as histamine and slow-reacting substances from mast cells. The role of mediator release in the induction of an asthmatic attack has been fully reviewed and documented, see Kaliner, M. and Austen, K. F., Bronchial Asthma Mechanisms and Therapeutics, E. B. Weiss, Editor, Little, Brown and Company, Boston, 1976, p. 163; Lichtenstein, L. M., Asthma-Physiology, Immunopharmacology and Treatment, Second International Symposium, L. M. Lichtenstein and K. F. Austen, Editors, Academic Press, New York, 1979, p. 51; and Bell, S. C., et al, Annual Reports in Medicinal Chemistry, 14, H. J. Hess, Editor, Academic Press, New York, 1979, p. 51.

The novel compounds of this invention as well as the prior art compound, 6-n-propyl-8-methylimidazo[1,5-d]-as-triazin-4(3H)-one, have been tested by the procedure of Lichtenstein, L. M. and Osler, A. G., J. Exp. Med., 120, 507–530, (1964), which evaluates the ability of compounds to inhibit mediator (histamine) release from immunologically stimluated human basophils.

REAGENTS

10X Concentrated Tris Buffer

Dissolve 140.3 g. of sodium chloride, 7.45 g. of potassium chloride and 74.5 g. of Trizma-Tris Pre-Set, Reagent Grade, pH 7.6, at 25° C. (Sigma Chemical Co.) in sufficient water to give a final volume of 2 liters.

Human albumin (Sigma Chemical Co.) (30 mg./ml.)

Calcium and Magnesium Stocks

Made to 0.075 M and 0.5 M. respectively, with calcium chloride dihydrate and magnesium chloride hexahydrate.

Tris-A-Buffer

A 10 ml. portion of 10X Tris Buffer and 1.0 ml. of human albumin are diluted to 100 ml. with water.

Tris ACM Buffer

A 10 ml. portion of 10X Tris Buffer, 1.0 ml. of human albumin. 0.8 ml. of calcium stock and 0.2 ml. of magnesium stock are diluted to 100 ml. with water.

Rabbit Antihuman IgE

Behring Diagnostics (Generally used at 10 µg. protein/ml. final concentration.)

House Dust Mite Extract (*Dermatophagoides Farinae*)

Strength 1:100 (w:v) allergenic extract, Hollister-Stier Labs. Generally this is diluted 1:1000 to 1:10,000 (considering the vial as stock).

OTHER ALLERGENS

Intradermal solutions or intramuscular preparations for hyposensitization, Hollister-Stier Labs. The final concentration used is on the order of 1 PNU/ml.

SEPARATION OF LEUKOCYTES FROM HUMAN BLOOD AND CHALLENGE

Eighty milliliters of blood is withdrawn from subjects with known histamine release to anti-IgE, ragweed antigen or other specific allergen, using four 20 ml. heparinized tubes. This 80 ml. of blood is mixed with 20 ml. of saline containing 0.6 g. of dextrose and 1.2 g. of dextran. The blood is allowed to sediment at room temperature in two 50 ml. polycarbonate centrifuge tubes until a sharp interface develops between the red cells and plasma (60–90 minutes). The plasma (top) layer from each tube is withdrawn by pipet and transferred to respective 50 ml. polycarbonate tubes. The plasma is centrifuged for 8 minutes at 110X g at 40° C. The supernatant is carefully poured off as completely as possible and the cell button is resuspended in 2–3 ml. of Tris-A buffer using a siliconized Pasteur pipet. The resuspension is accomplished by drawing the liquid gently in and out of the pipet, with the tip below the liquid, until an even suspension of cells is obtained. Sufficient Tris-A buffer is then added to bring the volume in the tube to about 45 ml. and the tube is centrifuged at 110X g for 8 minutes at 4° C. The supernatant is poured off and the cell button is resuspended and centrifuged as described above. The supernatant is poured off and the cell button is suspended in 2–3 ml. of Tris-ACM buffer and transferred to a siliconized or polycarbonate vessel with enough Tris-ACM buffer to make the final volume sufficient to allow addition to the reaction tubes.

Reaction tubes containing anti-IgE or antigens, either alone or with test compound in a total volume of 0.2 ml. are prepared and placed in a 37° C. bath. The cells are warmed to 37° C. and frequently swirled to ensure an even suspension, while 1.0 ml. aliquots are added to each reaction tube. The tubes are then incubated for 60 minutes at 37° C., vortexing the tubes gently every 15 minutes to keep the cells evenly suspended. When the reaction is complete, the tubes are centrifuged at 40° C. for 10 minutes at 1500 rpm. to sediment the cells. One ml. aliquots of supernatant are transferred to 12X 75 mm. polyethylene tubes and 0.2 ml. of 8% perchloric acid is added to each tube. Blanks and totals are included in each test. The blanks have cells and all reagents except antigen or anti-IgE. The totals contain 0.24 ml. of 8% perchloric acid, 1 ml. of cells and 0.2 ml. of buffer. All samples are then centrifuged to remove the precipitate protein.

ASSAY OF RELEASED HISTAMINE BY THE AUTOMATED FLUOROMETRIC METHOD

This automated method has been described by Siraganian, R. P., in Anal. Biochem., 57, 383 (1974) and J. Immunol. Methods, 7, 283 (1975) and is based on the manual method of Shore, P. A., et al., J. Pharmacol. Exp. Ther., 217, 182 ( 1959).

The automated system consists of the following Technicon Autoanalyzer II components: Sampler IV, Dual-Speed Proportioning Pump III, Fluoronephelometer with a narrow pass primary filter 7-60 and a secondary filter 3-74, Recorder, and Digital Printer. The manifold used is the one described by Siraganian vide supra, with the following modifications: the dialyzer is omitted; all pumping tubes pass through a single proportioning pump with large capacity and twice the volume of sample is taken for analysis.

The automated chemistry consists of the following steps: extraction from alkaline saline into butanol, back extraction into dilute hydrochloric acid by addition of heptane, reaction of histamine with o-phtaldialdehyde (OPT) at high pH and conversion of the OPT aduct to a stable fluorophore with phosphoric acid. The reaction product is then passed through the fluorometer. The full scale response is adjusted to 50 ng. histamine base with a threshold sensitivity of approximately 0.5 ng.

CALCULATION OF THE RESULTS OF HISTAMINE RELEASE TESTS

The instrument blank (wash) is subtracted from the ng. histamine of each sample. Then the ng. histamine of each sample is divided by the mean of the three totals (cells lysed with perchloric acid) to obtain percent release.

Control samples contain antigen but no test compound. Blank (or spontaneous release) samples contain neither antigen nor test compound. The mean of the blanks (three replicates) is subtracted from the percent release for controls and test compounds.

The means for control and test compound groups are computed and the result for a test compound is computed as percent of control by the formula:

$$100 \times \frac{\% \text{ Histamine Release with Test Compound}}{\% \text{ Histamine Release in Controls}}$$

Values obtained at different concentrations of test compound are used to calculate an ED50 (the concentration in µM which causes a 50% inhibition of histamine release) by linear regression.

The results of this test on typical compounds of this invention and the reference compound 6-n-propyl-8- methylimidazo[1,5-d]-as-triazin-4(3H)-one appear in Table I below.

TABLE I

| Compound | ED$_{50}$ μM |
| --- | --- |
| 1,8-Dimethyl-6-n-propylimidazo[1,5-d]-as-triazin-4(3H)—one | 13.1 |
| 1-Ethyl-6-n-propyl-8-methylimidazo[1,5-d]-as-triazin-4(3H)—one | 12.3 |
| 1,6-Di-n-propyl-8-methylimidazo[1,5-d]-as-triazin-4(3H)—one | 16.1 |
| 6-n-Propyl-8-methylimidazo[1,5-d]-as-triazin-4(3H)—one | 87 |

The novel compounds of the present invention are effective as anti-asthmatic agents in mammals when administered in amounts ranging from about 5 mg. to about 200 mg. per kilogram of body weight per day. A preferred dosage regimen for optimum results would be from about 5 mg. to about 50 mg. per kilogram of body weight per day, and such dosage units are employed that a total of from about 350 mg. to about 3.5 g. of the active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantages is that these active compounds may be administered in any convenient manner such as by the oral, intravenous, intramuscular, or subcutaneous routes.

The active compounds may be orally administered, for example, with an inert diluent or with as assimilable edible carrier, or they may be enclosed in hard or soft shell gelatin capsules, or they may be compressed into tablets, or they may be incorporated directly with the food of the diet. For oral therapeutic administration, these active compounds may be incorporated with excipients and used in the form of ingestible tablets, buccal tablets, troches, capsules, elixirs, suspensions, syrups, wafers, suppositories and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg. of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen of cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-released preparations and formulations.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol and polyethylene glycols. The polyethylene glycols consist of a mixture of non-volatile, normally liquid, polyethylene glycols which are soluble in both water and organic liquids and which have molecular weights of from about 200 to 1500. Although various mixtures of the aforementioned non-volatile polyethylene glycols may be employed, it is preferred to use a mixture having an average molecular weight of from about 200 to about 400.

In addition to the active compound, the parenteral solutions may contain various preservatives which may be used to prevent bacterial and fungal contamination. Such preservatives are, for example, myristyl-gamma picolinium chloride phenyl mercuric nitrate, benzalkonium chloride, phenethyl alcohol, p-chlorophenyl-α-glycerol ether, methyl and propyl parabens and thimerosal. As a practical matter, it is also convenient to employ anti-oxidants. Suitable antioxidants include, for example, sodium bisulfite, sodium metabisulfite and sodium formaldehyde sulfoxylate. Generally, from about 0.05 to about 0.2% concentrations of antioxidant are employed. These compounds may also be administered by inhalation using conventional Aerosol ® formulations.

The invention will be described in greater detail in conjunction with the following specific examples.

EXAMPLE 1

α,5-Dimethyl-2-n-propyl-4-imidazolemethanol

A 106.4 g. portion of 2-n-propyl-5-methyl-4-imidazolecarboxaldehyde (U.S. Pat. No. 4,107,307) is dissolved in 1400 ml. of tetrahydrofuran under argon at 0° C. and vigorously stirred while 429 ml. of 3 M methylmagnesium bromide are added over 20 minutes. The mixture is stirred at ambient temperature for 3.5 hours, then 900 ml. of 1.75 M hydrochloric acid are added to decompose the magnesium salts, giving the product as a white solid. The mixture is then saturated with solid ammonium chloride and the product is collected by filtration and air dried. The organic layer of the filtrate is concentrated in vacuo and the residue is triturated with a small portion of acetone, giving additional product. The crude product is dissolved in a minimum amount of ethanol and diluted with one volume of water, giving the desired compound as white crystals, m.p. 200°–202° C. (dec.).

EXAMPLE 2

Methyl 2-n-propyl-5-methyl-4-imidazolyl ketone

A suspension of 86.2 g. of α,5-dimethyl-2-n-propyl-4-imidazolemethanol in 2.16 liters of acetone is stirred in an ice bath and 430.9 ml. of Jones' reagent (120 g. of chromium trioxide, 257 ml. of water, 106.7 ml. of concentrated sulfuric acid, combined and diluted to 461.7 ml. with water) is dripped in at 20°–30° C. internal temperature over a period of one hour. Stirring is continued for 30 miuntes after the addition is complete, then 256 ml. of water were added. The reaction is then cooled in an ice bath and 256 ml. of 2-propanol are slowly added, maintaining the internal temperature at 20°-30° C. Stirring is continued for one hour, giving a suspension of solid and liquid. The liquid is decanted, concentrated to remove most of the acetone, and the aqueous residue is recombined with the solid. This mixutre is basified with concentrated aqueous potassium bicarbonate and an additional amount of solid potassium bicarbonate. The mixture is extracted with three 300 ml. portions of ethyl acetate. The extracts are combined, back washed with 100 ml. of saturated aqueous potassium bicarbonate dried over sodium sulfate and the solvent is removed in vacuo, giving the desired ketone which crystallizes on standing.

EXAMPLE 3

1,8-Dimethyl-6-n-propylimidazo[1,5-d]-as-triazin-4(3H)-one

A mixture of 59.7 g. of methyl 2-n-propyl-5-methyl-4-imidazolyl ketone, 41.14 g. of ethyl carbazate, 200 ml. of n-butanol and 4 drops of glacial acetic acid is warmed until solution is complete and then heated under reflux for 5 hours. The solution is concentrated in vacuo to an oily residue, 250 ml. of diphenyl ether are added and the resulting solution is heated with stirring in an oil bath for 30 minutes after the start of gas evolution. The temperature is maintained as closely as possible to the point at which gas evolution starts (150°-250°C.). The reaction is removed from the oil bath, cooled to 50° C. and diluted with 1-2 volumes hexane. The product is collected, washed with petroleum ether and then dissolved in 200 ml. of chloroform. This solution is filtered through 250 ml. of Magnesol ® followed by an 800 ml. chloroform wash. The filtrate is concentrated in vacuo and the residue is recrystallized from 250 ml. of ethyl acetate, giving 48.2 g. of the desired product as off-white crystals, m.p. 154°-155° C.

EXAMPLE 4

α-Ethyl-2-n-propyl-5-methyl-4-imidazolemethanol

The procedure of Example 1 is repeated using ethylmagnesium bromide in place of methylmagnesium bromide and giving the desired product, m.p. 193°-196° C. (dec.).

EXAMPLE 5

1-(2-n-Propyl-5-methyl-4-imidazolyl)-1-propanone

The procedure of Example 2 is repeated using an equimolar portion of α-ethyl-2-n-propyl-5-methyl-4-imidazolemethanol in place of α,5-dimethyl-2-n-propyl-4-imidazolemethanol and giving the desired product, m.p. 63°-67° C.

EXAMPLE 6

1-Ethyl-6-n-propyl-8-methylimidazo[1,5-d]-as-triazin-4(3H)-one

The procedure of Example 3 is repeated, using 1-2-n-propyl-5-methyl-4-imidzaolyl)-1-propanone in place of 2-n-propyl-5-methyl-4-imidazolyl ketone and giving the desired product, m.p. 147°-150° C.

EXAMPLE 7

α,2-Di-n-propyl-5-methyl-4-imidazolemethanol

The procedure of Example 1 is repeated using n-propylmagnesium bromide in place of methylmagnesium bromide and giving the desired product, m.p. 169°-171° C.

EXAMPLE 8 n-Propyl 2-n-propyl-5-methyl-4-imidazolyl ketone

The procedure of Example 2 is repeated using an equimolar amount of α,2-di-n-propyl-5-methyl-4-imidazolemethanol in place of α,5-dimethyl-2-n-propyl-4-imidazolemethanol and giving the desired product, m.p. 94°-95° C.

EXAMPLE 9

1,6-Di-n-propyl-8-methylimidazo[1,5-d]-as-triazin-4(3H)-one

The procedure of Example 3 is repeated using propyl 2-n-propyl-5-methyl-4-imidazolyl ketone in place of methyl 2-n-propyl-5-methyl-4-imidazolyl ketone and giving the desired product, m.p. 145°-146° C.

EXAMPLE 10

1,8-Dimethyl-6-n-propylimidazo[1,5-d]-as-triazin-4(3H)-one, monohydrate, monohydrochloride A 10.0 g. portion of 1,8-dimethyl-6-n-propylimidazo[1,5-d]-as-triazin-4(3H)-one is dissolved in 800 ml. of dichloromethane and treated with a stream of hydrogen chloride gas over a 30 minute period. The resulting precipitate is collected, slurried with two 60 ml. portions of dichloromethane and then dried in vacuo, giving 10.6 g. of the desired product as a while solid, m.p. 249°-255°C.

EXAMPLE 11

1-Ethyl-6-n-propyl-8-methylimidazo[1,5-d]-as-triazin-4(3H)-one, monohydrate, monohydrochloride The procedure of Example 10 is repeated using 1-ethyl-6-n-propyl-8-methylimidazo[1,5-d]-as-ytriazin-4(3H)-one in place of 1,8-dimethyl-6-n-propylimidazo[1,5-d]-as-triazin-4(3H)-one and giving the desired product, m.p. 236°-243° C.

EXAMPLE 12

1.6-Di-n-propyl-8-methylimidazo[1,5-d]-as-triazin-4(3H)-one, monohydrate, monohydrochloride The procedure of Example 10 is repeated using 1,6-di-n-propyl-8-methylimidazo[1,5-d]-as-triazin-4(3H)-one in place of 1,8-methyl-6-n-propylimidazo[1,5-d]-as-triazin-4(3H)-one and giving the desired product, m.p. 225° C. (dec.).

I claim:
1. A compound selected from the group consisting of those of the formula:

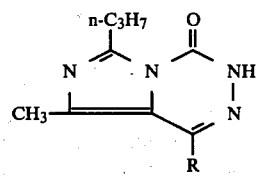

wherein R is methyl, ethyl or n-propyl; and the pharmaceutically acceptable acid-addition salts thereof.

2. The compound according to claim 1; 1,8-dimethyl-6-n-propylimidazo[1,5d]-as-triazin-4(3H)-one.

3. The compound according to claim 1; 1,8-dimethyl-6-n-propylimidazo[1,5-d]-as-triazin-4(3H)-one, monohydrochloride.

4. The compound according to claim 1; 1-ethyl-6-n-propyl-8-methylimidazo[1,5-d]-as-triazin-4(3H)-one.

5. The compound according to claim 1; 1-ethyl-6-n-propyl-8-methylimidazo[1,5d]-as-triazin-4(3H)-one, monohydrochloride.

6. The compound according to claim 1; 1,6-di-n-propyl-8-methylimidazo[1,5-d]-as-triazin-4(3H)-one.

7. The compound according to claim 1; 1,6-di-n-propyl-8-methylimidazo[1,5-d]-as-triazin-4(3H)-one, monohydrochloride.

* * * * *